United States Patent

Laske et al.

[11] Patent Number: 5,928,277
[45] Date of Patent: Jul. 27, 1999

[54] ONE PIECE DEFIBRILLATION LEAD CIRCUIT

[75] Inventors: Timothy G. Laske, Shoreview; David W. Mayer, Bloomington; Pedro A. Meregotte, Coon Rapids; Bret R. Shoberg, Corcoran; Gregory A. Boser, Richfield, all of Minn.

[73] Assignee: Medtronic, Inc., Minneapolis, Minn.

[21] Appl. No.: 09/026,064

[22] Filed: Feb. 19, 1998

[51] Int. Cl.$^6$ .................................................. A61N 1/05
[52] U.S. Cl. ......................................................... 607/122
[58] Field of Search .................................... 607/119, 122, 607/116; 600/373, 374

[56] References Cited

U.S. PATENT DOCUMENTS

| | | |
|---|---|---|
| 3,474,791 | 10/1969 | Bentov . |
| 4,481,953 | 11/1984 | Gold et al. ............................... 607/122 |
| 5,005,587 | 4/1991 | Scott . |
| 5,143,089 | 9/1992 | Alt . |
| 5,246,014 | 9/1993 | Williams et al. . |
| 5,336,254 | 8/1994 | Brennen et al. . |
| 5,360,442 | 11/1994 | Dahl et al. ............................... 607/119 |
| 5,584,873 | 12/1996 | Shoberg et al. . |
| 5,649,974 | 7/1997 | Nelson et al. ............................ 607/122 |
| 5,676,694 | 10/1997 | Boser et al. . |

*Primary Examiner*—William E. Kamm
*Assistant Examiner*—George R. Evanisko
*Attorney, Agent, or Firm*—Reed A. Duthler; Harold R. Patton

[57] ABSTRACT

An implantable electrical lead having a lead body with a longitudinal lumen therein and a stranded electrical conductor located in the lumen and which exits the lumen at a distal portion of the lead body, the distal end of the conductor being curved to form a loop and reentering the lumen, terminating within the lumen alongside a more proximal portion of the conductor. The portion of the conductor exterior to the lumen is wound around the lead body to form a coiled electrode. In some embodiments the distal end of the conductor is coupled to a more proximal portion of the conductor to form a loop and the loop is wound around the lead body to form a bifilar coil. In other embodiments the conductor is wound around the lead body to form a monofilar coil. The distal end of the conductor is mechanically and electrically coupled to a more proximal portion of the conductor, within the lumen.

4 Claims, 1 Drawing Sheet

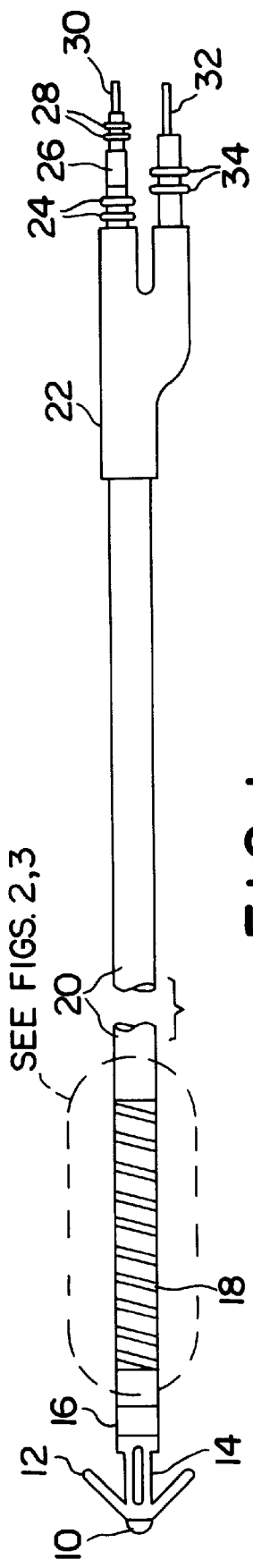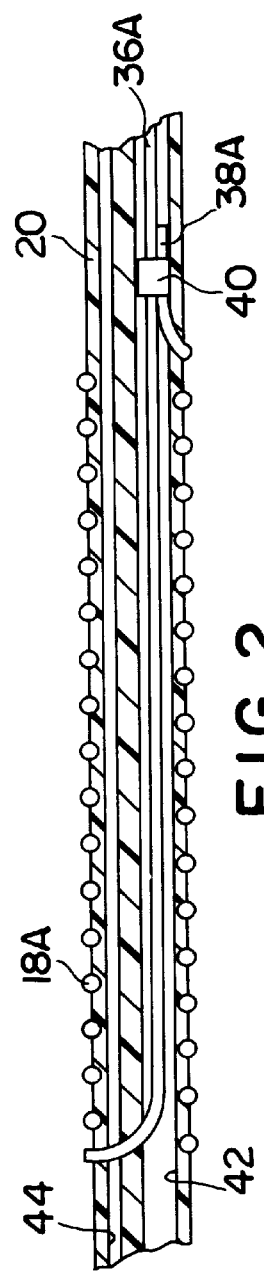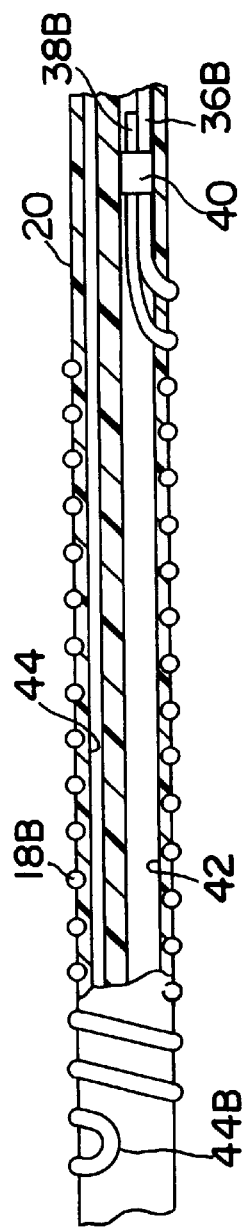

ONE PIECE DEFIBRILLATION LEAD CIRCUIT

BACKGROUND OF THE INVENTION

The present invention relates to implantable leads generally and more particularly to implantable cardioversion and defibrillation leads.

Commercially marketed implantable cardioversion and defibrillation leads often have employed cardioversion/defibrillation electrodes taking the form of elongated conductive coils mechanically coupled to elongated coiled conductors located within the lead body. More recently, there has been a renewed interest in stranded or cabled conductors in the context of implantable electrical leads. For example, such conductors are described in U.S. Pat. No. 5,584,873 issued to Shoberg et al. and in U.S. Pat. No. 5,246,014 issued to Williams et al. In the context of implantable cardioversion and defibrillation electrodes it has been proposed to employ extensions of the conductor within the lead body which are exposed to the exterior of the lead body as cardioversion or defibrillation electrodes. For example, U.S. Pat. No. 5,005,587 issued to Scott discloses the conductor in the form of a hollow metal braid, exposed to the exterior of the lead body over a length of the lead and useful as a defibrillation electrode. U.S. Pat. No. 5,143,089 issued to Alt and U.S. Pat. No. 5,336,254 issued to Brennan et al. disclose braided carbon fiber conductors which extend within the body of a defibrillation lead which also serve as cardioversion/defibrillation electrodes where they are exposed to the exterior of the lead body.

In currently manufactured cardioversion/defibrillation leads, it is not uncommon for the exposed electrode to be coupled to a separately formed coiled or stranded conductor at both ends of the exposed electrode coil. Such electrodes are illustrated in U.S. Pat. No. 5,676,694 issued to Boser et al.

SUMMARY OF THE INVENTION

The present invention is directed to an implantable cardioversion/defibrillation lead employing stranded or cabled conductors, for example as described in U.S. Pat. No. 5,584,873 issued to Shoberg, et al, incorporated herein by reference in its entirety. One of the stranded conductors also serves as the cardioversion/defibrillation electrode. The conductor exits the lead body laterally through an aperture formed therein and is wound around the lead body to form a coiled electrode. The distal end of the conductor is looped back so that it faces proximally and reenters the lead body, where it is mechanically and electrically coupled to a more proximal portion of the conductor, thus providing a redundant connection of the coil to the stranded or cabled conductor. By this expedient, a fracture of the exposed portion of the cabled conductor will not result in disconnection of any portion of the exposed coil from that portion of the conductor extending within the lead body.

In a first embodiment of the invention, the conductor is wound around the lead body in the form of a monofilar coil, with a portion of the conductor extending from the proximal end of the coil to the distal end of the coil within the lead body. In a second embodiment, the coil is wound as a bifilar coil, terminated at one end by means of a closed loop.

BRIEF DESCRIPTION OF THE DRAWINGS

FIG. 1 is a plan view of the lead according to the present invention.

FIG. 2 illustrates a cross-sectional view through a distal portion of a first embodiment of the lead according to the present invention.

FIG. 3 is a cross-sectional view through a distal portion of a second embodiment of a lead according to the present invention.

DETAILED DESCRIPTION OF THE PREFERRED EMBODIMENTS

FIG. 1 is a plan view of the lead according to the present invention. Pacing electrode 10 is located at the distal end of the lead, adjacent to tines 12 which extend from molded plastic tine sheath 14. Tines 12 are used to assist in maintaining pacing electrode 10 in the right ventricular apex. Any other form of pacing may be substituted for pacing electrode 10. Alternatively, pacing electrode 10 may simply be omitted, if the lead is to be employed in a portion of the heart which is not adjacent a cite desired for cardiac pacing. A second ring electrode 16 is shown located proximal to the tine sheath 14. In the embodiment illustrated, ring electrode 16 may be employed for bipolar pacing and/or sensing in conjunction with pacing electrode 10. Ring electrode 16 may similarly be omitted in some embodiments of the invention or replaced by an electrode similar in configuration to cardioversion/defibrillation electrode 18 but shorter in length.

Proximal to ring electrode 16 is cardioversion/defibrillation electrode 18 which, as described above, takes the form of a portion of an elongated cabled or stranded conductor wound helically around insulative lead body 20, which conductor extends proximally within insulative lead body 20 to connector assembly 22 where it is coupled to high voltage connector pin 32. Sealing rings 34 assist in sealing the connector port in which connector pin 32 is inserted from entry of bodily fluids. Connector assembly 22 also includes a connector pin 30 coupled to electrode 10 by means of an additional elongated conductor and connector ring 26 coupled to ring electrode 16 by means of a third elongated conductor within lead body 20. The sealing rings 24 and 28 seal the connector bore in which connector pin 30 and connector ring 26 are inserted against entry of fluids.

FIG. 2 illustrates a cross-sectional view through a distal portion of a first embodiment of the lead according to the present invention. As illustrated, lead body 20 takes the form of a multilumen lead body corresponding to that disclosed in the above cited Shoberg et al patent, which includes lumens for conductors, e.g., lumen 42 in which conductor 36A is located, as well as additional compression lumens such as lumen 44 which serve to assist the lead in avoiding damage due to applied compressive forces. The conductor 36A may take the form of a cabled conductor as described in the above-cited Shoberg et al. patent, comprised of seven strands, six of which are wound around the seventh strand, each strand formed of seven wires. The wires employed to form the cabled conductor are preferably highly conductive, and may for example be formed with a highly conductive core metal such as copper or silver, provided with an outer surface of a biocompatible second metal such as platinum, iridium, rhodium, palladium or alloys thereof or the like. In particular, silver cored wires with outer surfaces of platinum or platinum-iridium alloy may usefully be employed.

The lead illustrated corresponds to that illustrated in FIG. 1, with defibrillation electrode 18A taking the form of a portion of elongated cabled conductor 36A which exits lead body 20 laterally at the distal end of the intended location of electrode 18A, and extends proximally from that point in a monofilar coil wound about and preferably slightly embedded into the outer surface of lead body 20. At the proximal end of the defibrillation electrode, the distal end of the conductor 36A reenters lead body 40 and is coupled to a more proximal portion of the conductor by 36A by means of a conductive crimping sleeve 40. Alternatively, the conductor 36A might exit the lead body at the intended proximal end of the electrode extending distally along the lead body in the form of a monofilar coil, returning to an interior lumen of the lead body to be coupled to a more proximal portion of the conductor by means of crimp sleeve 40.

In this embodiment, a redundant connection is provided to the exposed portion 18A which constitutes the cardioversion or defibrillation electrode so that any fracture of the conductor along the length of coil 18A will not disconnect a portion of the electrode from the remainder of the conductor 36A located within the lead body. In addition, the cardioversion/defibrillation electrode is coupled at both of its end to the conductor within the lead body with a minimum of complexity, in turn reducing the over-all cost of the lead.

FIG. 3 is a cross-sectional view through a distal portion of a second embodiment of a lead according to the present invention. The lead of FIG. 3 corresponds to that illustrated in FIGS. 1 and 2 generally, with identically labeled components corresponding exactly to the components in the previous drawings. However, in this embodiment, the cardioversion or defibrillation electrode 18B takes the form of a bifilar coil with a closed loop end 44B, rather than taking it from a monofilar coil. The bifilar coil is produced by crimping the distal end 38B of elongated cable connector 36B to a more proximal portion of the conductor to form a loop. The looped conductor exits a lateral portion of insulative lead body 20 at the point intended to be the proximal end of the cardioversion/defibrillation electrode and extends distally therefrom, wound around the lead body 20 in the form of a bifilar coil. The looped end 44B of the conductor is adhered to or embedded within lead body 20 in order to stabilize it.

While the above illustrated embodiments of leads according to the present invention take the form of endocardial defibrillation leads, the invention is believed applicable in all cardioversion and defibrillation leads employing bundled or stranded conductors which require electrodes taking the form of an exposed coil extending along a length of an elongated insulative lead body, which may also of course include epicardial and subcutaneous cardioversion/defibrillation electrodes. As such, the above disclosure should be taken as illustrative rather than limiting in conjunction with the claims that follow.

In conjunction with the above disclosure, we claim:

1. An implantable electrical lead, comprising:

an elongated insulative lead body having a longitudinal lumen therein extending from a proximal end of the lead body to a distal portion of the lead body;

an electrical connector mounted to the proximal end of the lead body;

an elongated stranded electrical conductor located in the lumen, the conductor having a proximal end coupled to the electrical connector and a distal end which exits the lumen at the distal portion of the lead body and is wound around the lead body in a coil and thereafter reenters the lumen and is mechanically and electrically coupled to a more proximal portion of the conductor within the lumen.

2. An implantable electrical lead, comprising:

an elongated insulative lead body having a longitudinal lumen therein extending from a proximal end of the lead body to a distal portion of the lead body;

an electrical connector mounted to the proximal end of the lead body;

an elongated stranded electrical conductor located in the lumen, the conductor having a proximal end coupled to the electrical connector and a distal end which exits the lumen at the distal portion of the lead body and reenters the lumen and is coupled to a more proximal portion of the conductor in the lumen, forming a loop, and wherein the loop is wound around the lead body in a bifilar coil.

3. An implantable electrical lead, comprising:

an elongated insulative lead body having a longitudinal lumen therein extending from a proximal end of the lead body to a distal portion of the lead body;

an electrical connector mounted to the proximal end of the lead body;

an elongated stranded electrical conductor located in the lumen, the conductor having a proximal end coupled to the electrical connector and a distal end which exits the lumen at the distal portion of the lead body is wound around the lead body in a coil and thereafter reenters the lumen and extends within the lumen to a point where the conductor is coupled to a more proximal portion of the conductor within the lumen.

4. A lead according to claim 1 or claim 2 or claim 3 wherein the stranded conductor is a cabled conductor.

* * * * *